(12) United States Patent
Yoneda et al.

(10) Patent No.: US 11,629,324 B2
(45) Date of Patent: Apr. 18, 2023

(54) CELL TREATMENT SYSTEM

(71) Applicant: SHIBUYA CORPORATION, Kanazawa (JP)

(72) Inventors: Kenji Yoneda, Kanazawa (JP); Naoya Deguchi, Kanazawa (JP); Noriaki Nishimura, Kanazawa (JP)

(73) Assignee: SHIBUYA CORPORATION, Kanazawa (JP)

( * ) Notice: Subject to any disclaimer, the term of this patent is extended or adjusted under 35 U.S.C. 154(b) by 115 days.

(21) Appl. No.: 17/001,903

(22) Filed: Aug. 25, 2020

(65) Prior Publication Data
US 2021/0062134 A1 Mar. 4, 2021

(30) Foreign Application Priority Data

Aug. 26, 2019 (JP) .............................. JP2019-154138

(51) Int. Cl.
  *C12M 3/00* (2006.01)
  *C12M 1/12* (2006.01)
  *C12M 1/00* (2006.01)

(52) U.S. Cl.
  CPC ............ *C12M 37/00* (2013.01); *C12M 23/04* (2013.01); *C12M 23/50* (2013.01)

(58) Field of Classification Search
  CPC .............................. C12M 37/00; C12M 41/14
  See application file for complete search history.

(56) References Cited

U.S. PATENT DOCUMENTS

| | | | | |
|---|---|---|---|---|
| 4,262,091 A | * | 4/1981 | Cox .......................... | B01L 1/04 435/253.6 |
| 5,861,305 A | * | 1/1999 | Silley ..................... | C12M 41/14 435/286.6 |
| 9,395,282 B2 | * | 7/2016 | Kobayashi ................ | B01L 1/02 |
| 2003/0040104 A1 | * | 2/2003 | Barbera-Guillem ... | C12M 23/48 435/286.2 |
| 2006/0151185 A1 | * | 7/2006 | Takagi .................... | C12M 41/48 172/4 |
| 2020/0025782 A1 | * | 1/2020 | Ahlfors ..................... | B01L 1/04 |

FOREIGN PATENT DOCUMENTS

JP  201838309 A  3/2018

* cited by examiner

*Primary Examiner* — Nathan A Bowers
(74) *Attorney, Agent, or Firm* — Flynn Thiel, P.C.

(57) ABSTRACT

To continue a series of cell treatments even in a case where a treatment has become impossible in any isolator, a cell treatment system is provided with at least two isolators that perform different treatments, such that a sequential series of cell treatments is performed in each of the isolators. The cell treatment system is provided with a first isolator that performs a first treatment, a second isolator that performs a second treatment different from the first treatment, and a common isolator capable of performing the first treatment and the second treatment.

4 Claims, 1 Drawing Sheet

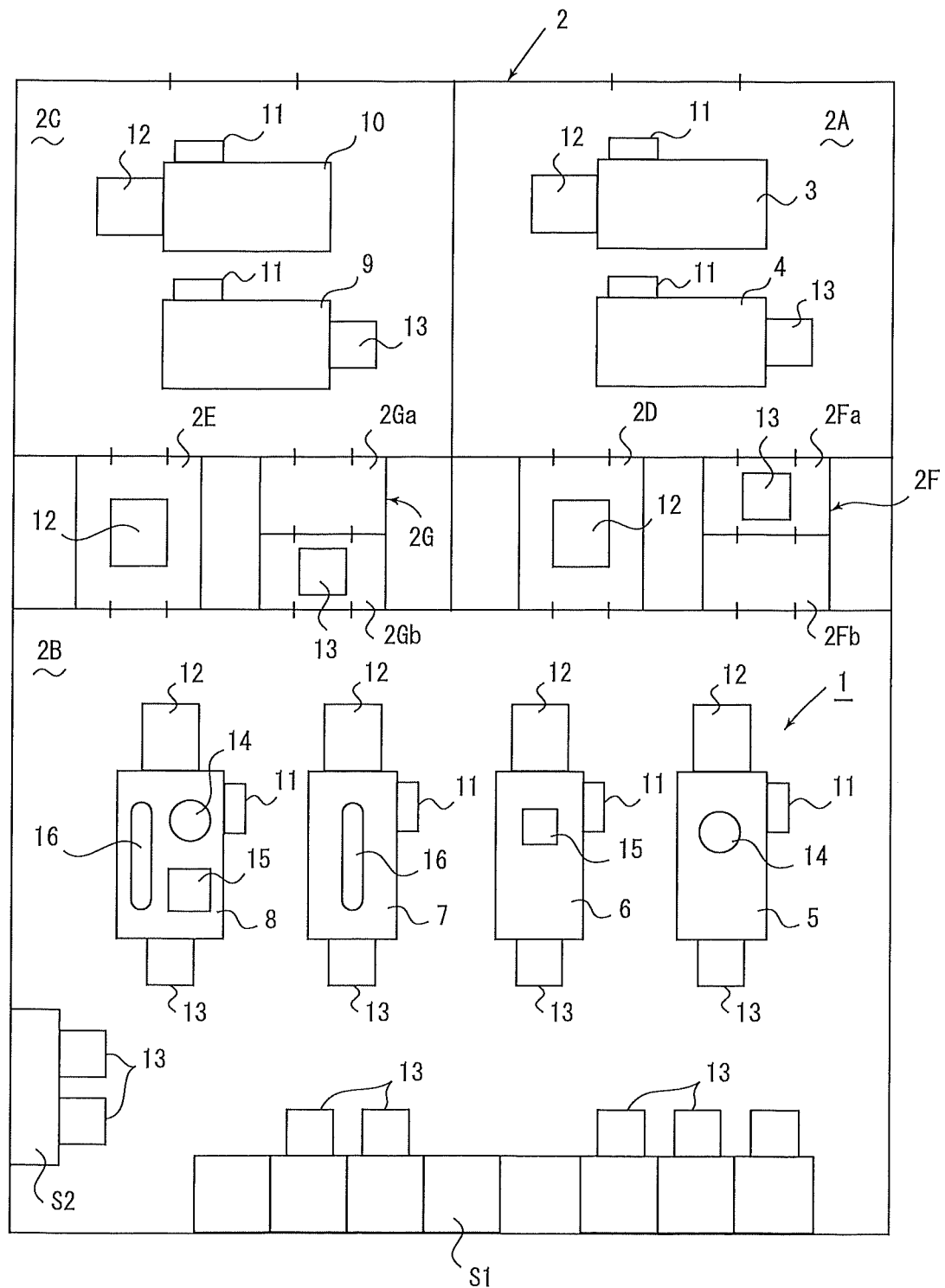

CELL TREATMENT SYSTEM

BACKGROUND OF THE INVENTION

Field of the Invention

The present invention relates to a cell treatment system, and more particularly, relates to a cell treatment system provided with a plurality of isolators that perform different treatments, such that different treatments associated with cell manipulation are performed in a sterile environment in each isolator.

Description of the Related Art

Currently, medical therapy using cells is being performed, and the cells used in such medical therapy need to be cultivated and grown outside the body after being collected from a patient.

To perform such cell cultivation efficiently, there is a cell treatment system provided with a plurality of isolators that perform different treatments, and by performing different treatments in each of the isolators, a series of cell treatments associated with cell manipulation is divided into a plurality of steps (Patent Literature 1).

CITATION LIST

Patent Literature

Patent Literature 1: Japanese Patent Laid-Open No. 2018-38309

SUMMARY OF THE INVENTION

In the cultivation treatment system according to Patent Literature 1, a series of cell treatments for cell manipulation is handled in a distributed manner by a plurality of cultivation vessels, but if a fault in an internal treatment means or some other kind of trouble occurs in any one of the cultivation vessels, the cell treatments in the other cultivation vessels must be discontinued. As a result, there is a problem in that the work thus far and the cells become wasted, such as by having to dispose of partially cultivated cells.

In light of such a problem, the present invention provides a cell treatment system provided with at least two isolators that perform different treatments associated with cell manipulation in a sterile environment, such that a sequential series of cell treatments is performed in each of the isolators. Even if a treatment becomes impossible in one of the isolators, the cell treatment system is capable of continuing the series of cell treatments.

More specifically, the cell treatment system according to a first aspect of the present invention is a cell treatment system provided with at least two isolators that perform different treatments in association with cell manipulation in a sterile environment, such that a sequential series of cell treatments is performed in each of the isolators, the cell treatment system being characterized by comprising:

a first isolator that performs a first treatment in association with the cell manipulation, a second isolator that performs a second treatment different from the first treatment, and a common isolator capable of performing the first treatment and the second treatment, characterized in that when a treatment becomes impossible in either the first or second isolator, the common isolator performs the treatment of the isolator where the treatment has become impossible.

According to the present invention, by providing a common isolator capable of performing the first treatment and the second treatment, even in the case where a treatment has become impossible in either the first isolator or the second isolator, the series of cell treatments can be continued.

BRIEF DESCRIPTION OF THE DRAWING

FIG. 1 is a plan view of a cell processing facility in which a cell treatment system is installed.

DETAILED DESCRIPTION OF THE PREFERRED EMBODIMENT

To describe the illustrative example below, FIG. 1 illustrates a plan view of a cell processing facility 2 in which a cell treatment system 1 according to the present invention is installed.

According to the cell treatment system 1 of the present example, it is possible to cultivate a variety of cells as cell manipulation for instance, but a plurality of treatments are needed to cultivate any of the cells.

For instance, cells targeted for cultivation are extracted from blood or a body fluid collected from a patient, and it is necessary to perform treatments such as a seeding treatment that seeds the target cells in a cultivation vessel, a medium replacement treatment that replaces the medium in a cultivation vessel where cells are being cultivated, a subculturing treatment that subcultures cells that have been cultivated to a certain degree in another cultivation vessel, and a collection treatment that collects cultivated cells from a cultivation vessel.

The cell processing facility 2 is provided with a materials supply chamber 2A for preparing materials used in the cultivation of cells, a cell manipulation chamber 2B where the cells are cultivated, and a cell collection chamber 2C for collecting the cultivated cells.

The internal spaces of the materials supply chamber 2A, the cell manipulation chamber 2B, and the cell collection chamber 2C are partitioned in an airtight state with respect to the outside space around the cell processing facility 2, and furthermore are maintained at a higher level of cleanliness than the outside space. Among the chambers, the cell manipulation chamber 2B is maintained at a higher level of cleanliness than the materials supply chamber 2A and the cell collection chamber 2C, and is also maintained at a positive pressure.

In addition, the space between the cell manipulation chamber 2B and the materials supply chamber 2A as well as the space between the cell manipulation chamber 2B and the cell collection chamber 2C are provided with material passing rooms 2D and 2E for passing a transfer vessel 12 containing materials to be described later, and cell passing rooms 2F and 2G for passing a container 13 containing cells.

The material passing room 2D is provided with openable and closable doors that communicate with the materials supply chamber 2A and the cell manipulation chamber 2B, such that the interior of the material passing room 2D is set to a higher air pressure than the materials supply chamber 2A and a lower air pressure than the cell manipulation chamber 2B.

Similarly, the material passing room 2E is provided with openable and closable doors that communicate with the cell manipulation chamber 2B and the cell collection chamber 2C, such that the interior of the material passing room 2E is set to a lower air pressure than the cell manipulation chamber 2B and a higher air pressure than the cell collection chamber 2C.

Furthermore, the material passing rooms 2D and 2E are provided with a decontaminating means for decontaminating the internal spaces of the rooms with a decontamination medium such as hydrogen peroxide vapor, which makes it possible to decontaminate the outer surface of the transfer vessel 12.

The cell passing room 2F is provided with openable and closable doors that communicate with the materials supply chamber 2A and the cell manipulation chamber 2B, and is also internally provided with a partition wall having an openable and closable door that partitions the room into a space 2Fa near the materials supply chamber 2A and a space 2Fb near the cell manipulation chamber 2B.

The space 2Fa near the materials supply chamber 2A is set to a higher air pressure than the materials supply chamber 2A, while the space 2Fb near the cell manipulation chamber 2B is set to a higher air pressure than the space 2Fa near the materials supply chamber 2A and also a lower air pressure than the cell manipulation chamber 2B.

Similarly, the cell passing room 2G is also partitioned by a partition wall, and a space 2Ga near the cell collection chamber 2C is set to a higher pressure than the cell collection chamber 2C, while a space 2Gb near the cell manipulation chamber 2B is set to a higher air pressure than the space 2Ga near the cell collection chamber 2C and also a lower air pressure than the cell manipulation chamber 2B.

The materials supply chamber 2A is provided with a materials supply isolator 3 for preparing materials to use in the cultivation of cells and a cell preparation isolator 4 for preparing cells to cultivate.

The cell manipulation chamber 2B is provided with a first isolator 5 that performs the seeding treatment, a second isolator 6 that performs the medium replacement treatment, and a third isolator 7 that performs the subculturing treatment.

Furthermore, in case a treatment becomes impossible in any of the first to third isolators 5 to 7, the cell manipulation chamber 2B is provided with a common isolator 8 capable of performing the seeding treatment, the medium replacement treatment, and the subculturing treatment.

The cell manipulation chamber 2B is also provided with a cultivation station S1 which is connected to the container 13 described later and which is for cultivating cells contained in the container 13, and a decontamination station S2 for decontaminating the container 13.

Additionally, the cell collection chamber 2C is provided with a cell collection isolator 9 for collecting cultivated cells and a materials collection isolator 10 for collecting and disposing of used materials.

In the present example, the interior of each isolator is maintained in a sterile state, and cell manipulation such as the work of cultivating cells can be performed in a sterile environment.

Because the isolators themselves are known in the related art, a detailed description is omitted here, but the isolators are configured such that the internal space of each isolator is maintained in a sterile state, and gloves to be worn by a worker for performing work inside the internal space are also provided on a side face of each isolator.

Furthermore, each isolator is provided with a decontamination device 11 for decontaminating the internal space with a decontamination medium such as hydrogen peroxide vapor, making it possible to decontaminate the internal space with the decontamination device 11 after the cultivation of cells for a certain patient is completed.

Also, in the cell treatment system 1 according to the present example, to transfer cells from isolator to isolator in a sterile environment, each isolator is provided with the transfer vessel 12 and the container 13 which are removably connectible to each isolator while maintaining a sterile state.

The transfer vessel 12 is used to transfer materials from the materials supply isolator 3 of the materials supply chamber 2A to another isolator, while the container 13 is configured as an incubator capable of containing cells in each cultivation vessel inside.

Because a connecting means for connecting the transfer vessel 12 or the container 13 to each isolator is known in the related art, a detailed description is omitted, but a connecting means that connects the materials supply isolator 3 and the transfer vessel 12 will be described here as an example.

Openings that are openable and closable by doors are formed in the materials supply isolator 3 and the transfer vessel 12, while in addition, coupling members are provided to surround the openings.

When the coupling members are coupled together, a space partitioned from the outside is formed between the openings, making it possible to supply a decontamination member to the space from the decontamination device 11 and decontaminate the space.

When the decontamination finishes, opening the doors of the materials supply isolator 3 and the transfer vessel 12 causes the internal space of the materials supply isolator 3 and the internal space of the transfer vessel 12 to communicate with each other while maintaining the sterile state, making it possible to move materials and the like.

Note that in the present example, the opening in the transfer vessel 12 is larger than the opening in the container 13, and the connecting position of the transfer vessel 12 is different from the connecting position of the container 13, but the sizes of the openings may also be made uniform and the openings may be connected at the same connecting positions.

In the following description of each isolator, the materials supply isolator 3 provided in the materials supply chamber 2A is used to distribute materials needed for cell cultivation to the other isolators.

The materials for cultivating cells include cultivation vessels such as Petri dishes, flasks, and well plates, as well as centrifuge tubes and pipettes used with devices such as dispensers and aspirators.

When materials transported into the materials supply chamber 2A from outside the cell processing facility 2 are contained, inside the materials supply isolator 3, the decontamination device 11 fills the materials supply isolator 3 with the decontamination medium, thereby decontaminating the outer surfaces of the materials.

Next, the materials are contained in the transfer vessel 12 connected in advance, and thereafter, the transfer vessel 12 is disconnected from the materials supply isolator 3, placed inside the material passing room 2D provided between the materials supply chamber 2A and the cell manipulation chamber 2B, and the outer surface of the transfer vessel 12 is decontaminated.

After that, if the door on the cell manipulation chamber 2B side of the material passing room 2D is opened, the transfer vessel 12 can be moved into the cell manipulation chamber 2B and connected to a necessary isolator.

Next, the cell preparation isolator 4 provided in the materials supply chamber 2A is an isolator for preparing supplied cells in a state suited to cultivation work. Additionally, the container 13 is connectible to the cell preparation isolator 4.

To describe the work of passing cells from the cell preparation isolator 4 to another isolator, first, a worker carries a vessel containing cells from outside the cell processing facility 2, and the vessel or the like is contained inside the cell preparation isolator 4.

When preparation work of preparing and containing a cell suspension in a vessel, such as a centrifuge tube, in the cell preparation isolator 4 finishes, the vessel is contained in the container 13 connected in advance, and thereafter, the container 13 is disconnected from the cell preparation isolator 4 and placed inside the cell passing room 2F provided between the materials supply chamber 2A and the cell manipulation chamber 2B.

Initially, the container 13 is contained in the space 2Fa near the materials supply chamber 2A, and the container 13 is bathed in alcohol or the like in a state with the doors closed. In other words, in consideration of the effects on the cells due to the time taken for decontamination, the container 13 containing the cells is not decontaminated using a decontamination medium such as hydrogen peroxide vapor, but instead, the outer surface of the container 13 is disinfected with a disinfectant such as alcohol.

After that, the container 13 is moved to the space 2Fb near the cell manipulation chamber 2B, the door on the cell manipulation chamber 2B side is opened in a state in which the door on the space 2Fa side is closed, and the container 13 is moved from the space 2Fb to the cell manipulation chamber 2B.

At this point, the doors are opened and closed during this work, but because a pressure of the each room is different, it is possible to prevent the intrusion of the outside environment into the cell manipulation chamber 2B as much as possible.

The first isolator 5 provided in the cell manipulation chamber 2B is used to perform the seeding treatment of seeding the cells contained in the centrifuge tube and transported in the cell suspension state into a cultivation vessel.

A seeding device 14 acting as a first treatment device that performs the seeding treatment is provided inside the first isolator 5, and although a detailed procedure of the seeding treatment and a detailed description of the seeding device 14 are omitted here, as an example, the seeding device 14 is configured as a dispenser that supplies and drains the medium and the cell suspension, an aspirator or a centrifuge that removes liquid by suction, a moving means that moves the centrifuge tube or the cultivation vessel between the dispenser, the aspirator, and the centrifuge, or the like. The seeding device 14 is controlled by a controlling means not illustrated.

The second isolator 6 is used to perform the medium replacement treatment that replaces the medium in the cultivation vessel containing seeded cells.

A medium replacement device 15 acting as a second treatment device is provided inside the second isolator 6, and although a detailed procedure of the medium replacement treatment and a detailed description of the medium replacement device 15 are omitted here, as an example, the medium replacement device 15 is configured as a aspirator that removes medium from the cultivation vessel by suction, a dispenser that supplies new medium into the cultivation vessel, a cleaning solution supplying means that supplies a cleaning solution, a moving means that moves the centrifuge tube or the cultivation vessel between the aspirator, the dispenser, and the cleaning solution supplying means, or the like. The medium replacement device 15 is controlled by a controlling means not illustrated.

The third isolator 7 is used to perform the subculturing treatment that distributes cells grown by cultivation to a plurality of cultivation vessels.

A subculturing device 16 acting as a third treatment device is provided inside the third isolator 7, and although a detailed procedure of the subculturing treatment and a detailed description of the subculturing device 16 are omitted here, the subculturing device 16 is configured as a dispenser that supplies and drains the medium and the cell suspension, an aspirator or a centrifuge that removes liquid by suction, a cleaning solution supplying means that supplies a cleaning solution, a moving means that moves the centrifuge tube or the cultivation vessel between the dispenser, the aspirator, the centrifuge, and the cleaning solution supplying means, or the like. The subculturing device 16 is controlled by a controlling means not illustrated.

The cultivation vessels containing cells treated in the first to third isolators 5 to 7 in this way are thereafter moved to the cultivation station S1 in a state of being contained in the container 13.

If the first to third isolators 5 to 7 and the container 13 are made to communicate using the connecting means while maintaining the sterile state, the cultivation vessels containing the cells treated in the isolators are contained in the container 13.

Subsequently, the container 13 is connected to the cultivation station S1 after separating from each isolator, and because the container 13 is configured as an incubator, electric power, carbon dioxide, and the like are supplied from the cultivation station S1 to each container 13, and the interior of the container 13 is maintained in an environment suited to cultivating cells.

Additionally, by connecting the container 13 to the cultivation station S1 for a predetermined period, cells are cultivated inside the container 13.

Furthermore, when a treatment becomes impossible in any of the first to third isolators 5 to 7, the common isolator 8 according to the present example is used to perform the treatment instead of the isolator where the treatment has become impossible.

Described specifically, the common isolator 8 is provided with the same seeding device 14 as the first isolator 5, the same medium replacement device 15 as the second isolator 6, and the same subculturing device 16 as the third isolator 7, and consequently the isolator forming the common isolator 8 is larger than the isolators forming the first to third isolators 5 to 7.

While the series of cell treatments are being performed normally in the first to third isolators 5 to 7, the common isolator 8 is maintained in a standby state, but if a treatment becomes impossible in any of the isolators, in order to pass the cultivation vessels containing cells to the common isolator 8: the container 13 is connected to the isolator where the treatment has become impossible; the cells being treated are contained in the container 13; and the container 13 is connected to the common isolator 8.

Similarly, in the case where a treatment becomes impossible in one of the isolators that performs a post-cultivation treatment on cells being cultivated in the cultivation station S1, the container 13 is connected to the cultivation station S1, the cells whose cultivation period has ended are contained in the container 13, and the container 13 is connected to the common isolator 8.

Next, in the common isolator 8, the cells are carried in from the container 13, the same treatment device as the treatment device of the isolator where the treatment has become impossible is activated, and the treatment performed in the isolator where the trouble has occurred is performed.

At this point, by configuring the controlling means of the first to third isolators 5 to 7 to be communicable with the controlling means of the common isolator 8, the controlling means can automatically determine the operation that was being performed when the treatment becomes impossible, and continue the treatment.

Note that it is not strictly necessary to install the same seeding device 14, medium replacement device 15, and subculturing device 16 as the first to third isolators 5 to 7 in the common isolator 8, and it is sufficient for the common isolator 8 to be provided with the dispenser, the aspirator, the centrifuge, the cleaning solution supplying means, and the like that form the above devices, and for the common isolator 8 to be configured to execute the same treatments.

The cell collection isolator 9 provided in the cell collection chamber 2C is an isolator for collecting cultivated cells from the cultivation vessels, and in the present example, a collection treatment is performed manually by a worker.

First, the container 13 is disconnected from the cultivation station S1 of the cell manipulation chamber 2B, and the container 13 is contained in the cell passing room 2G provided between the cell manipulation chamber 2B and the cell collection chamber 2C.

Initially, the container 13 is contained in the space 2Gb near the cell manipulation chamber 2B, but in a procedure similar to the cell passing room 2F, the outer surface of the container 13 is bathed in alcohol or the like, and then the container 13 is moved to the space 2Ga near the cell collection chamber 2C.

After that, if the container 13 is moved to the cell collection chamber 2C and connected to the cell collection isolator 9, the cultivation vessels containing the cells are moved to the cell collection isolator 9, and the cultivated cells are collected, while in addition, the work of aggregating the cells into a single collection vessel is performed.

Additionally, when the cells are aggregated into a single vessel, the vessel is sealed, and then a worker takes the vessel out of the cell collection isolator 9 and also carries the vessel from the cell collection chamber 2C to outside the cell processing facility 2.

Note that the cell collection isolator 9 may also be internally provided with a collection device including a dispenser, aspirator, or some other means and be configured to perform the collection treatment automatically. In this case, the common isolator 8 may also be provided with the collection device, and in the case where a treatment has become impossible in the cell collection isolator 9, the collection treatment may be performed in the common isolator 8.

To dispose of materials such as cultivation vessels and pipettes used in each isolator, the materials collection isolator 10 provided in the cell collection chamber 2C is an isolator for collecting such materials into a disposal bag or the like, and is connectible to the transfer vessel 12.

At this point, when the transfer vessel 12 is connected to each isolator of the cell manipulation chamber 2B, the transfer vessel 12 is used to pass the materials contained in the materials supply isolator 3 to the isolators and also receive used materials.

When the treatment in each isolator finishes, the transfer vessel 12 is disconnected from each isolator and thereafter contained in the material passing room 2E provided between the cell manipulation chamber 2B and the cell collection chamber 2C, and the outer surface of the transfer vessel 12 is decontaminated by a decontamination medium.

After that, when the transfer vessel 12 is moved to the cell collection chamber 2C and connected to the materials collection isolator 10, a worker collects the used materials inside the transfer vessel 12 into a disposal bag or the like, and after the collection is finished, the outer surface of the bag is decontaminated again.

Additionally, when a predetermined quantity of materials has been collected into a bag, the bag is sealed, and after that, a worker takes the bag out of the materials collection isolator 10 and also carries the bag from the cell collection chamber 2C to outside the cell processing facility 2.

In addition, the transfer vessel 12 and the container 13 used when cultivating cells are connected to the decontamination station S2 provided in the cell manipulation chamber 2B after each is used.

The decontamination station S2 is configured as a decontamination device that supplies a decontamination medium to decontaminate the internal spaces of the transfer vessel 12 and the container 13 when connected to the decontamination station S2.

According to the present example, even in the case where a treatment becomes impossible in any of the first to third isolators 5 to 7, the same treatment as the isolator where the treatment has become impossible can be performed in the common isolator 8, thereby making it possible to continue cell manipulation without an interruption in the series of cell treatments, and wasting of cells is avoided.

Note that in the present example, the container 13 is configured as an incubator, but the container 13 may also be configured as a simple storage vessel and the cultivation station S1 may be configured as an incubator. In this case, the cultivation station S1 and the container 13 are configured to be removably connectible while maintaining a sterile state using the connecting means described above like the means that connects each isolator to the container 13, and the container 13 passes cultivation vessels from each isolator to the cultivation station S1 for cultivation.

Also, the container 13 may be provided with a purification filter such as a HEPA filter and may be configured to allow air to pass to and from the outside while maintaining an internal sterile state, thereby making it possible to cultivate cells by carrying the container 13 still storing the cultivation vessels into the incubator, that is, the cultivation station S1.

Also, in the present example, the first to third isolators 5 to 7 are provided as isolators that perform predetermined cell treatments necessary for cell manipulation, but it is also possible to perform cell manipulation configured by different treatments for purposes other than cultivating cells, and the number of isolators may be increased or decreased accordingly. Also, the configuration of each treatment device provided inside each isolator may be modified to suit the treatments.

What is claimed is:

1. A cell treatment system provided with at least three isolators that perform different treatments in association with cell manipulation in a sterile environment such that a sequential series of cell manipulation treatments is performed in each of the isolators, the cell treatment system comprising:
   a first isolator having an interior and a seeding device disposed in the interior and configured to perform a cell seeding treatment;
   a second isolator having an interior and a medium replacement device disposed in the interior of the second isolator and configured to perform a medium replacement treatment for seeded and cultivated cells;

a third isolator having an interior and a subculturing device disposed in the interior of the third isolator and configured to perform a subculturing treatment including distributing cultivated and proliferated cells; and a common isolator having an interior and at least one treatment device disposed in the interior of the common isolator and configured to perform the same seeding treatment performed by the seeding device of the first isolator, configured to perform the same medium replacement treatment performed by the medium replacement device of the second isolator, and configured to perform the same subculturing treatment performed by the subculturing device of the third isolator, the common isolator being maintained in a standby state while a series of cell manipulation treatments is performed in the first isolator, the second isolator and the third isolator, the first isolator, the second isolator and the third isolator being in informational communication with the common isolator and the common isolator being configured to automatically determine a treatment being performed in any of the first isolator, the second isolator or the third isolator based on the informational communication and to activate the at least one treatment device to perform the same treatment in the common isolator when treatment becomes impossible in the first isolator, the second isolator or the third isolator.

2. The cell treatment system according to claim 1, further comprising a container removably connectible to the first isolator, the second isolator, the third isolator and the common isolator while maintaining a sterile state, and cells are passed to the common isolator from the first isolator, the second isolator and the third isolator using the container.

3. The cell treatment system according to claim 2, further comprising an incubator connected to the container, the incubator being configured for containing and cultivating cells after each treatment performed by the seeding device, the medium replacement device and the subculturing device.

4. The cell treatment system according to claim 1, wherein the at least one treatment device of the common isolator comprises three treatment devices, a first of the three treatment devices comprising a seeding device configured to perform the same cell seeding treatment as the seeding device of the first isolator, a second of the three treatment devices comprising a medium replacement device configured to perform the same medium replacement treatment as the medium replacement device of the second isolator and a third of the treatment devices comprising a subculturing device configured to perform the same subculturing treatment as the subculturing device of the third isolator.

* * * * *